US009726616B2

(12) United States Patent
Mathon et al.

(10) Patent No.: US 9,726,616 B2
(45) Date of Patent: Aug. 8, 2017

(54) MACHINE FOR WEAVING OR WINDING A FIBER TEXTURE AND ENABLING ANOMALIES TO BE INSPECTED BY IMAGE ANALYSIS

(71) Applicant: SNECMA, Paris (FR)

(72) Inventors: Richard Mathon, Brunoy (FR); Sylvain Corradini, Port sur Saone (FR); Jean-Francois Durand, Baraqueville (FR)

(73) Assignee: SNECMA, Paris (FR)

( * ) Notice: Subject to any disclaimer, the term of this patent is extended or adjusted under 35 U.S.C. 154(b) by 107 days.

(21) Appl. No.: 14/787,142

(22) PCT Filed: Apr. 18, 2014

(86) PCT No.: PCT/FR2014/050956
§ 371 (c)(1),
(2) Date: Oct. 26, 2015

(87) PCT Pub. No.: WO2014/174193
PCT Pub. Date: Oct. 30, 2014

(65) Prior Publication Data
US 2016/0077019 A1 Mar. 17, 2016

(30) Foreign Application Priority Data
Apr. 26, 2013 (FR) .................... 13 53888

(51) Int. Cl.
*G01N 21/898* (2006.01)
*D03D 51/08* (2006.01)
(Continued)

(52) U.S. Cl.
CPC .......... *G01N 21/898* (2013.01); *B65H 26/02* (2013.01); *B65H 63/065* (2013.01); *D03D 51/08* (2013.01);
(Continued)

(58) Field of Classification Search
CPC ............... B29C 70/32; F01D 21/045; G01N 2021/8472; G01N 2021/8854;
(Continued)

(56) References Cited

U.S. PATENT DOCUMENTS 5,224,047 A * 6/1993 Kitagawa ............... B65H 63/00
57/264
6,299,730 B1 * 10/2001 Broek .................... B65H 26/02
162/198
(Continued)

FOREIGN PATENT DOCUMENTS

WO 2012 140355 10/2012

OTHER PUBLICATIONS

International Search Report Issued Jul. 15, 2014 in PCT/FR14/050956 Filed Apr. 18, 2014.

*Primary Examiner* — Gordon J Stock, Jr.
(74) *Attorney, Agent, or Firm* — Oblon, McClelland, Maier & Neustadt, L.L.P.

(57) ABSTRACT

A machine for weaving or winding a fiber preform on a mandrel having an axis of rotation that is substantially horizontal and that serves to receive the preform, the machine having a plurality of cameras pointing towards the underside of the fiber preform in order to scan the hidden face of the fiber preform and acquire images of the hidden face; an image analysis module for processing these images of the hidden face of the fiber preform in a plurality of adjacent scan windows, and for extracting weaving patterns therefrom and comparing them with reference weaving patterns previously stored in the module; a motor for driving the mandrel in rotation about its axis of rotation; and a control unit for stopping rotation of the mandrel if the result of the comparison reveals a difference of appearance between the two weaving patterns.

10 Claims, 5 Drawing Sheets (51) Int. Cl.
*D03J 1/00* (2006.01)
*D06H 3/12* (2006.01)
*D06H 3/08* (2006.01)
*B65H 63/06* (2006.01)
*B65H 26/02* (2006.01)
*G01N 21/89* (2006.01)
*G01N 21/84* (2006.01)
*F01D 21/04* (2006.01)
*B29C 70/32* (2006.01)

(52) U.S. Cl.
CPC ............... *D03J 1/004* (2013.01); *D03J 1/007* (2013.01); *D06H 3/08* (2013.01); *D06H 3/12* (2013.01); *G01N 21/8903* (2013.01); *B29C 70/32* (2013.01); *F01D 21/045* (2013.01); *G01N 2021/8472* (2013.01)

(58) Field of Classification Search
CPC ... G01N 2021/8858; G01N 2021/8861; G01N 2021/8867; G01N 2021/887; G01N 2021/8887; G01N 2021/888; G01N 2021/8909; G01N 21/8903; G01N 21/898; G01N 21/8983; G01N 21/88; G01N 21/8803; G01N 21/8806; G01N 21/8851; G01N 21/89; G01N 21/8901; G01N 21/894; B65H 26/02; B65H 26/025; B65H 26/066; B65H 63/00; B65H 63/003; B65H 63/006; B65H 63/0324; B65H 63/06; B65H 63/065; D06H 3/00; D06H 3/02; D06H 3/06; D06H 3/08; D06H 3/12; D06H 3/124; D03J 1/004; D03J 1/007; D03D 51/08; D03D 51/085; D03D 51/007
See application file for complete search history.

(56) References Cited

U.S. PATENT DOCUMENTS

| | | | |
|---|---|---|---|
| 6,633,383 B1* | 10/2003 | Jackson | B65H 63/006 356/238.2 |
| 6,725,123 B1 | 4/2004 | Denuell | |
| 6,741,726 B1* | 5/2004 | Nevel | G01B 11/105 356/429 |
| 7,310,565 B2* | 12/2007 | Vergote | D03D 51/18 139/318 |
| 7,819,355 B2* | 10/2010 | Prittie | B65H 16/06 226/118.2 |
| 8,506,758 B2* | 8/2013 | Ruuska | B65H 26/025 162/263 |
| 9,403,325 B2* | 8/2016 | Corradini | B65H 23/0328 |
| 9,499,926 B2* | 11/2016 | Cohen | D03J 1/007 |
| 2002/0054694 A1* | 5/2002 | Vachtsevanos | G01N 21/956 382/111 |
| 2002/0109112 A1* | 8/2002 | Guha | G01N 21/89 250/559.46 |
| 2004/0049310 A1* | 3/2004 | Morimoto | D03D 51/007 700/140 |
| 2005/0078306 A1 | 4/2005 | Engels | |
| 2007/0271064 A1 | 11/2007 | Walton | |
| 2014/0027046 A1 | 1/2014 | Mathon et al. | |

\* cited by examiner

MACHINE FOR WEAVING OR WINDING A FIBER TEXTURE AND ENABLING ANOMALIES TO BE INSPECTED BY IMAGE ANALYSIS

BACKGROUND OF THE INVENTION

The present invention relates to the general field of making gas turbine casings out of composite material, and more particularly fan retention casings for aeroengine gas turbines.

It is common practice for a fan retention casing to be constituted by a relatively thin wall that defines the passage for admitting air into the engine and that supports an abradable material in register with the path followed by the tips of the fan blades, that possibly also supports a sound treatment coating, and that supports a shield structure that is fastened to the outside of the wall over the fan in order to retain debris, such as items that have been ingested or fragments of damaged blades that are projected by centrifuging, for the purpose of preventing them from passing through the casing and reaching other portions of the aircraft.

Proposals already exist to make a fan retention casing out of composite material. By way of example, reference may be made to Document EP 1 961 923, which describes fabricating a casing out of composite material of varying thickness, which method comprises forming fiber reinforcement as superposed layers of a fiber texture and densifying the fiber reinforcement with a matrix. More precisely, that document provides for using a takeup mandrel for the three-dimensional weaving of the fiber texture, which texture is then wound as superposed layers on an impregnation mandrel of profile that corresponds to the profile of the casing to be fabricated. The preform as obtained in that way is held on the impregnation mandrel and it is impregnated with resin, which resin is then polymerized.

It should nevertheless be observed that during the winding operation, a portion of the preform (more precisely its bottom face) is not visible to operators who are situated on a work platform that is conventionally located above the winder machine. That configuration thus prevents various anomalies being detected that might affect the preform, such as pollution (adhesive tape, cut fibers, . . . ) or weaving faults in the portion of the preform that cannot be visually inspected by the operators. Unfortunately, this winding operation is the last step in the fabrication process where such anomalies can still be detected. Thus, if they are not identified during winding, they are hidden by being covered in the superposition of layers of the preform.

It is important to observe that these anomalies that are situated on the hidden face of the preform during the winding operation, are also not detectable during the prior weaving operation since they are likewise hidden while weaving on a loom, for example.

Consequently, there exists a need to have a winding machine or a weaving machine (or loom) that makes it possible to detect both pollution and weaving faults on the hidden face of the preform prior to any winding. After winding, it is impossible to inspect for such contamination and faults of the preform and it is then impossible to validate the winding operation.

OBJECT AND SUMMARY OF THE INVENTION

A main object of the present invention is thus to mitigate such a need by providing a solution for repairing or rejecting the preform prior to the impregnation stage. Another object of the invention is to enable data concerning the positions, the occurrences, and the types of anomalies to be subjected to statistical analysis in order to monitor the quality of the weaving and/or winding operations.

These objects are achieved with a method of determining weaving anomalies in a machine for weaving or winding a fiber preform onto a mandrel having an axis of rotation that is substantially horizontal for the purpose of receiving the preform, the mandrel being driven about the axis of rotation by a motor actuated by a control unit; in which method a plurality of cameras looking at the underside of the fiber texture scan the hidden face of the fiber preform and acquire images of the hidden face, and an image analysis module processes the images of the hidden face of the fiber preform in a plurality of adjacent scan windows in order to extract weaving patterns therefrom and compare them with reference weaving patterns previously stored in the module, and the control unit stops rotation of the mandrel if the result of the comparison reveals, in at least one scan window, a difference in appearance between the two weaving patterns that is characteristic of the presence of an anomaly resulting from pollution and/or weaving faults in the fiber preform, and when an anomaly is recognized, its position on the fiber preform and a label selected by an operator from predetermined types of anomaly are stored together with an image of said anomaly, and when the recognized anomaly is repaired, a corresponding label selected by an operator from predetermined types of repair is stored together with an image of said repair, and the recognized anomalies and the repaired anomalies are displayed in a developed representation or a three-dimensional representation of said fiber preform that is accessible to the operator from said control unit.

By performing real time analysis of the images of the fiber preform in a plurality of scan windows, it is possible to monitor for any pollution or faults in the weaving pattern and to correct the weaving or winding operations that have been performed, or to invalidate them, should that be necessary. This results in a machine that is well adapted to making fan retention casings out of composite material for aeroengines. In particular, the operation of the machine can be fully automated, thereby contributing to reducing the fabrication cycle time for such casings.

Preferably, the sizes, the positions, and the number of scan windows are defined by the operator directly on images coming from the cameras.

Advantageously, the number of scan windows corresponds at most to the number of cameras pointing towards the fiber preform.

Preferably, the plurality of cameras are mounted in a light box adapted to match the profile of said mandrel and placed as close as possible to said fiber preform, the light box delivering blue light at a wavelength lying in the range 446 nanometers (nm) to 500 nm, or red light at a wavelength lying in the range 620 nm to 800 nm.

Advantageously, said appearance difference results from examining gray level curves for the images from the cameras.

In the intended implementation, said examination is performed in each of the scan windows along at least one detection line or else on a predefined detection area.

The invention is applicable both in a weaving machine where said mandrel is a takeup mandrel and in a winding machine where said mandrel is an impregnation mandrel.

BRIEF DESCRIPTION OF THE DRAWINGS

Other characteristics and advantages of the present invention appear from the following description made with reference to the accompanying drawings, which show embodiments having no limiting character, and in which.

DETAILED DESCRIPTION OF EMBODIMENTS

The invention is described below in the context of its application to fabricating a fan retention casing for a gas turbine aeroengine, and an example implementation is described in Document EP 1 961 923, to which reference may be made.

The casing is made of a composite material having fiber reinforcement densified by a matrix. The reinforcement is made of fibers, e.g. carbon, glass, aramid, or ceramic fibers, and the matrix is made of polymer, e.g. an epoxy, bismaleimide, or polyimide resin.

Briefly, the fabrication method described in that document consists in beginning by making a fiber texture by three-dimensional weaving with the texture being taken up in the warp direction on a mandrel having a profile that is determined as a function of the profile of the casing to be fabricated.

Figure 1A:
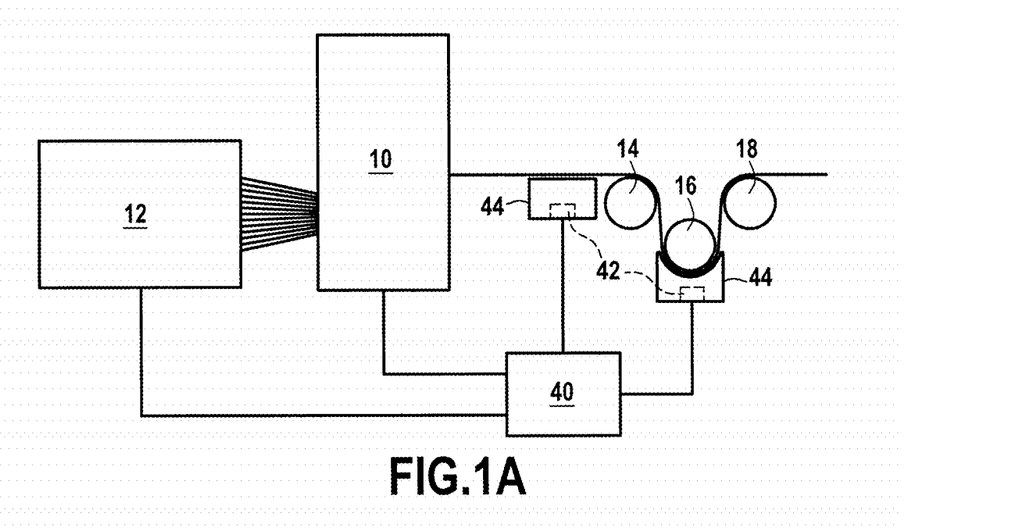
FIGS. 1A and 1B are two diagrams showing respectively a loom and a winding machine.

FIG. 1A shows such a fiber texture being obtained by weaving on a Jacquard type loom 10 that is fed by a warp yarn feed center 12 and that delivers the fiber texture onto a pull mandrel 14, which fiber texture is subsequently transported to the winding machine via various other support mandrels such as a reverse mandrel 16 or a takeup mandrel 18. The takeup mandrel may constitute the takeup mandrel of the winding machine shown in FIG. 1B.

Once the fiber texture or preform has been woven it is somewhat like a dry mat and it is delivered onto a takeup mandrel for subsequent transfer and winding in a plurality of turns (typically four turns plus a turn fraction of less than ¼ of a turn) on the mandrel of a resin injection mold (referred to below as the impregnation mandrel) having an outside profile that corresponds to the inside profile of the casing to be fabricated.

While the preform is being held on the impregnation mandrel, it is impregnated with a resin. For this purpose, a casing is formed by applying a plurality of parts in combination with the preform, and the resin is injected into the mold as constituted in this way. Impregnation may be assisted by setting up a pressure difference between the inside and the outside of the mold in which the preform is contained. After impregnation, a step of polymerizing the resin is performed.

Figure 1B:
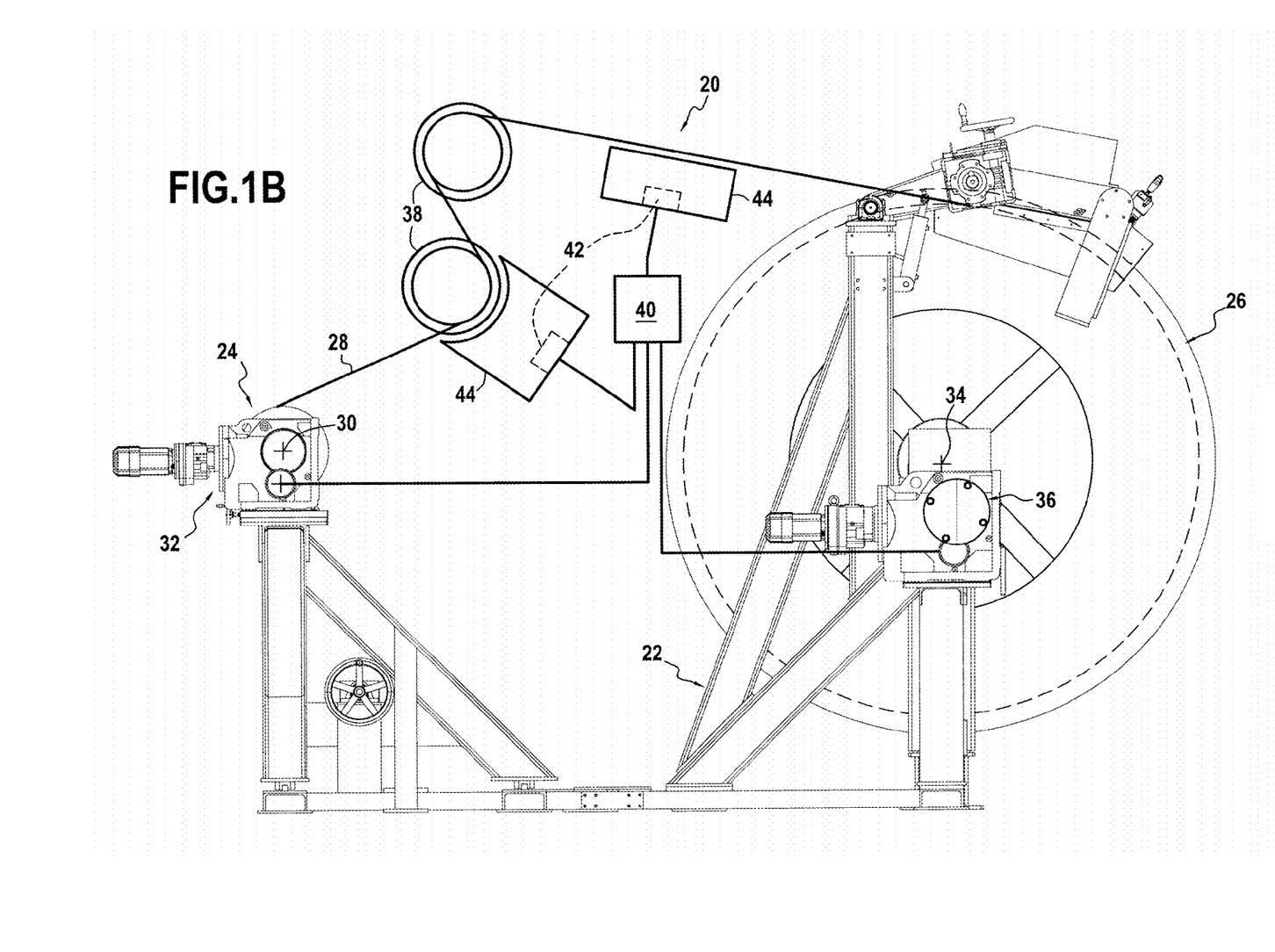

The winding machine 20 making this possible, while also performing real time monitoring of the alignment and possible off-centering of the preform, itself comprises a stand 22 supporting in particular the takeup mandrel 24 and the impregnation mandrel 26. The takeup mandrel 24 that receives the preform 28 as obtained by three-dimensional weaving is carried by a horizontal shaft 30 having one end rotatably mounted on the stand 22 of the winding machine and having its other end coupled to the outlet shaft of a first motor 32. The impregnation mandrel 26 for receiving superposed layers of the preform as unwound from the takeup mandrel and that presents an outside surface of profile corresponding to the profile of the inside surface of the casing that is to be made is itself carried by a horizontal shaft 34 that is parallel to the axis of rotation 30 of the takeup mandrel and that has one end rotatably mounted on the stand 22 while its other end is coupled to the outlet shaft of a second motor 36. Forming rolls 38 may be provided between the takeup mandrel and the impregnation mandrel.

A control unit 40 is connected to the motors 32 and 36 in order to control and monitor the speed of rotation of each mandrel. In more general terms, the control unit conventionally organized around a central processor unit 400, memory modules 402, and input/output modules 404 (in particular for interfacing with a screen 406, a keyboard 408, etc.) (see FIG. 2) serves to control all of the operating parameters of the winding machine, both while putting the preform into place (calibration stage) and then while it is being wound (automatic control stage).

The invention makes provision for automatically detecting any anomaly as from engagement and throughout the winding operation (and also during the prior weaving operation) of the preform prior to engaging the impregnation stage. The proposed solution consists in putting a plurality of cameras 42 into place that are associated with an image analysis module and that are positioned on the winding machine (or the loom) beneath the preform so as to be able to take images of the hidden face of the preform while it is traveling, thus making it possible to detect possible anomalies from which it might be suffering. The equipment is capable of characterizing the surface of a preform and of comparing it with reference weaving patterns that are thus known as being fault-free references. This mapping of faults makes it possible in real time to recognize faults automatically and enables the operator to be given information about how critical a fault is. In particular, it is possible to inform the operator on the action to be taken when a fault appears (e.g.: stop winding for analysis, continue winding, act on the preform in order to make a repair as a function of the detected fault, . . . ) or else to locate accurately all of the faults so as to identify their three-dimensional (3D) positions on the casing in order to make it possible, at the end of winding, to verify that they are not too close together and that they are not likely to impact the soundness of the part, or indeed so as to generate a time-varying fault catalog in order to refine detection.

More particularly, in order to show up the weaving pattern of the preform and in order to be unaffected by the interfering light produced by workshop lighting, the cameras are placed in a light box 44 that is preferably placed as close as possible to the preform during winding, so as to isolate the surface of the preform from ambient or interfering lighting in the workshop above the machine.

In FIGS. 1A and 1B, various locations in which the light box 44 might be installed are shown as examples. It can thus be observed that when the light box is arranged facing a mandrel, it is preferably shaped to match the profile of the mandrel.

Furthermore, in order to increase the contrast presented by the weaving pattern of the woven preform made of carbon fibers, and thus enhance identification of various types of anomaly, it is advantageous to use either blue light (wavelength lying in the range 446 nm to 500 nm), or else red light (wavelength lying in the range 620 nm to 800 nm).

Figure 2:
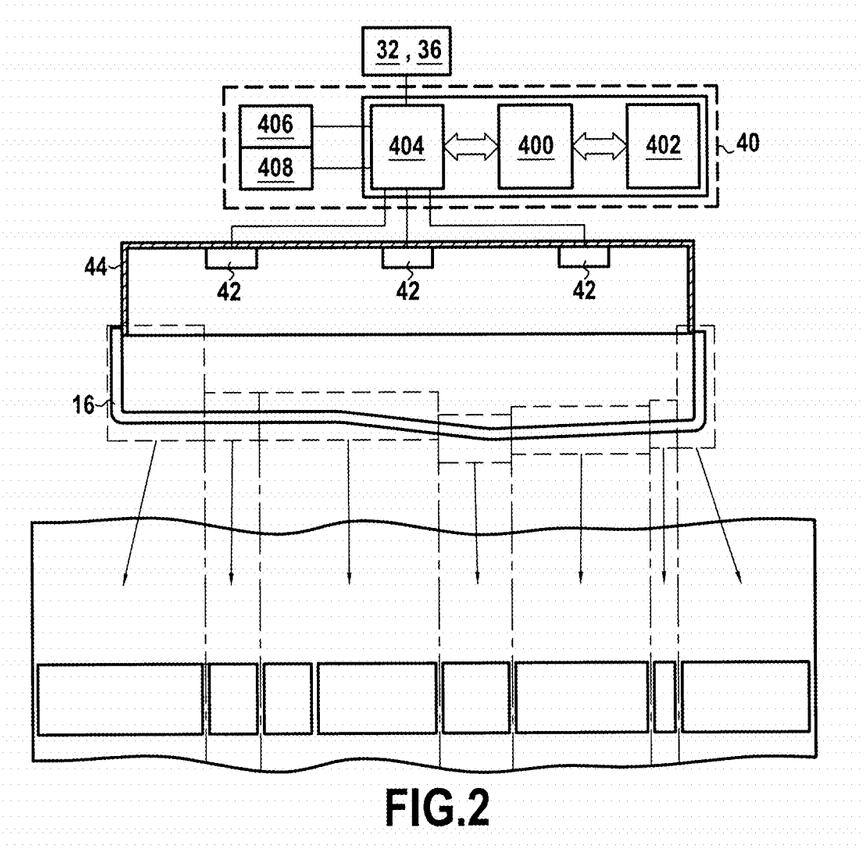
FIG. 2 is a view showing the principle of multizone monitoring of a preform in the invention.

As shown in FIG. 2, the image analysis module that is advantageously incorporated in the control unit 40 is itself capable of simultaneously monitoring a plurality of zones of the preform from images delivered by the cameras, and to distinguish between the weaving patterns from each of them by detecting differences of preform appearance compared with reference weaving patterns preferably recorded in the module, and in order to send a signal to the operator to enable the operator to take action in the event of a mismatch, and in particular to stop the travel of the preform if the result of comparing two weaving patterns reveals, in at least one of the monitored zones, a difference in appearance that is characteristic of the presence of an anomaly resulting from pollution and/or faults in weaving the preform. The sizes, positions, and numbers of monitored zones are defined by the operator using scan windows in the image analysis module so as to fully cover a strip extending over the entire width of the preform. Advantageously, in order to obtain uniform weaving patterns, such scan windows are selected to lie on either side of tracer yarns that are woven in the preform. Each camera is allocated to a determined zone of the preform and can therefore cover one or more scan windows.

Figure 3:
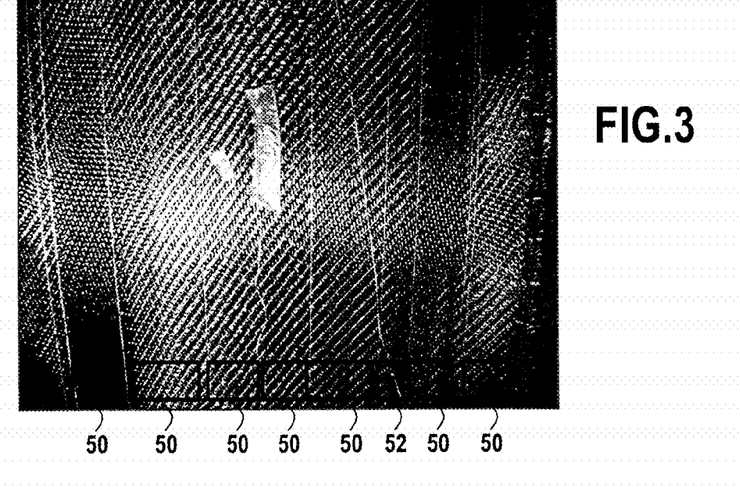
FIG. 3 is a view showing an image displayed on the monitor screen of the devices shown in FIG. 1A or 1B.

For this purpose, and as shown in FIG. 2, the operator acts during a stage of initializing the system (when starting weaving or winding) to create these scan windows directly on the image of the preform by using a graphics software tool specific to the image analysis module. These windows are preferably selected to lie in a strip of the preform that is believed to be sound, i.e. without pollution or faults. When the operator views the presence of a sound preform zone in each scan window on the monitor screen 406, the operator validates a step that may be referred to as "reference taking" and the validated weaving pattern appearing in the zone is stored (for a given strip of the preform, FIG. 3 shows examples of sound zones 50 that are to be validated and zones 52 that are not sound and that cannot be validated). The pattern difference is the result of variations in the weaving of each zone of the preform. The stored data is a map of gray levels in the image. Since the weaving pattern is repetitive, it is possible with this measure to use the gray levels in the image of the preform in order to obtain a gray level curve that is likewise repetitive. During the winding or weaving operations, any variation in the appearance of the gray level curve is then interpreted as an anomaly.

Figure 4:
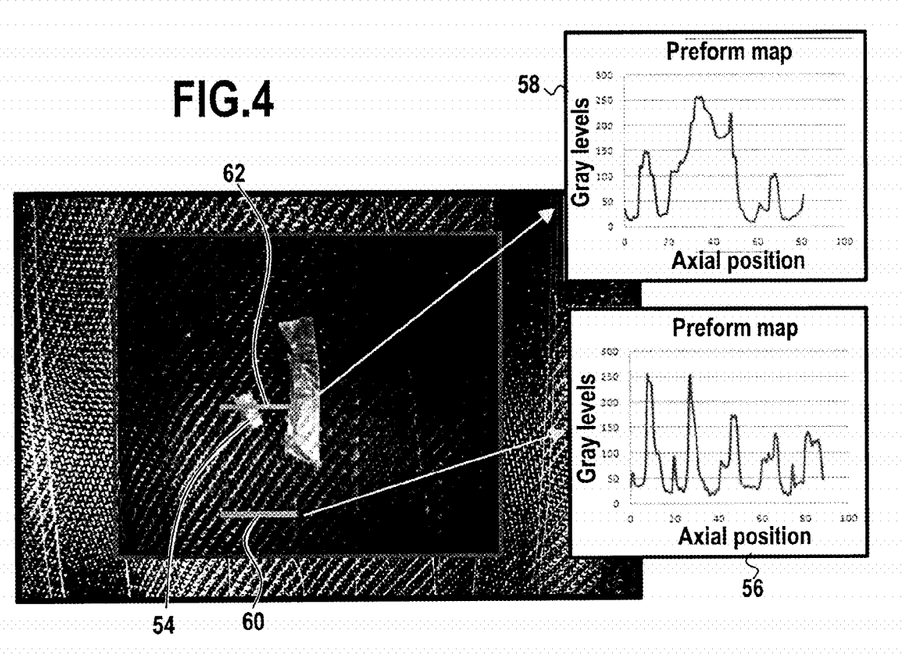
FIG. 4 is a detail view of an anomaly.

An example of detecting pollution is shown in FIG. 4, specifically a piece of adhesive tape 54 forgotten by an operator when putting the preform into place on the winding machine. It can clearly be seen in the figure that, in comparison with the reference weaving pattern for the zone 56 in question, there is a variation in the weaving pattern of the preform as a result of analyzing the gray level curve 58. This type of detection makes it possible to detect anomalies of the pollution type (Scotch® tape, Kevlar® fiber, short fibers, . . . ) and also most weaving faults such as warp float, weft float, a long float or "misweave", loops, a broken tracer yarn, a broken warp yarn, a missing yarn or "pick", a double yarn or "pick", a partially missing yarn (partially missed pick), a fuzzy yarn, . . . . In the example shown, the mode of detection is described as being along a detection line (broad horizontal lines 60, 62), however the module is naturally capable of monitoring variation in the weaving pattern over a detection area equivalent to the scan window so as to provide the most sensitive possible detection mode, if necessary. A detection threshold in terms of gray level and axial position can also be set in order to accommodate "normal" variations in the weaving pattern.

Figure 5:
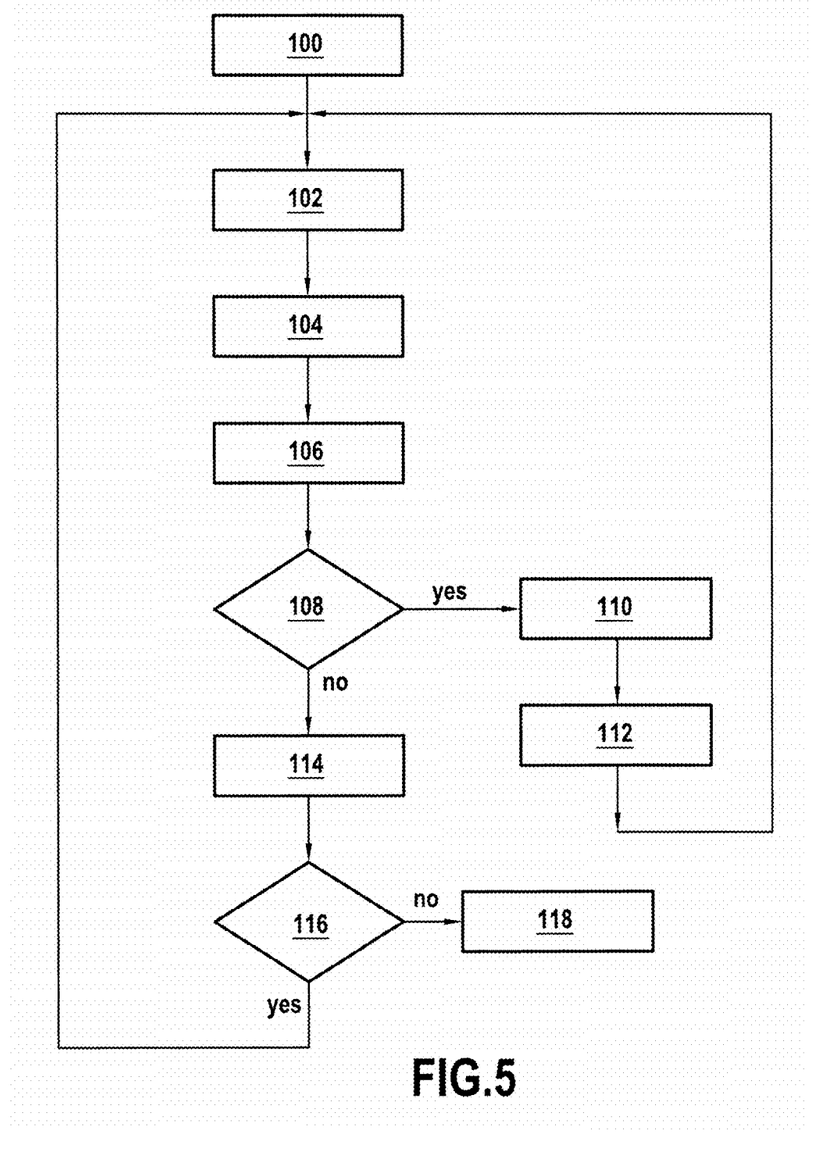
FIG. 5 shows the various steps of the method of the invention.
Figure 6A:
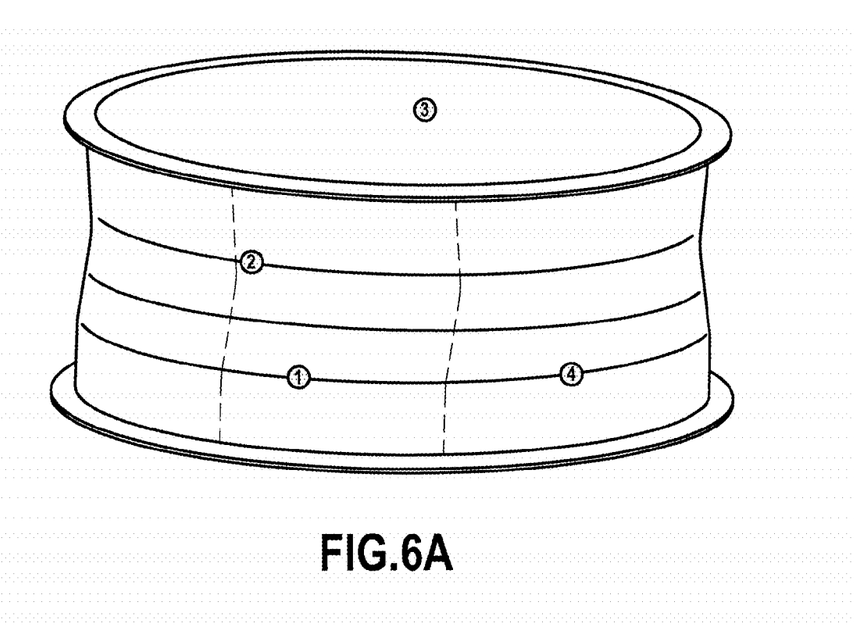
FIGS. 6A and 6B are respectively a perspective view and a developed view of an example of the distribution of defects on a fan blade.
Figure 6B:
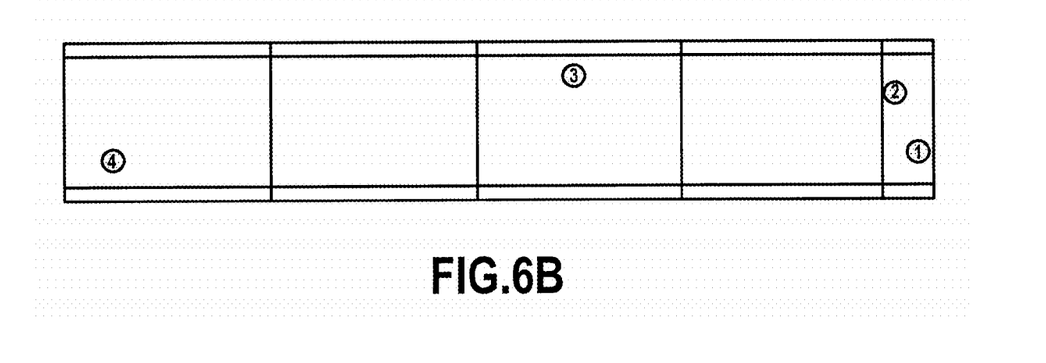

The various steps performed for processing anomalies and analyzing them statistically in order to track the quality of weaving and/or winding operations are described below with reference to FIG. 5 in the example of a winding machine. Once the initialization stage has been completed (step 100), the winding of the preform is engaged (step 100) and continues until the image analysis module detects an anomaly (step 102). On the appearance of this anomaly, the winding operation is stopped and the monitor screen is frozen on the detected anomaly. The anomaly is automatically given an order number and its position is then stored together with an image of the anomaly, and the operator is invited to select a label for the anomaly from the various types of anomaly that have previously been stored (step 104). The operator can then intervene directly on the preform to look directly at the anomaly (step 106) and then determine whether it can be repaired (test of step 108). If the answer to this test is "yes", the repair is carried out (step 110) and it is automatically given a repair order number which is then stored together with an image of the repair that has been undertaken, and the operator is invited to select a label for the repair from the various types of repair that have previously been stored (step 112). Winding can then be restarted (return to step 102 for detecting possible new anomalies). If the answer to the test in step 108 is "no", it is then necessary to call on an expert (step 114) to decide whether the anomaly is critical (test of step 116), i.e. of a nature that requires winding to be stopped (step 118) and the preform to be rejected, or else on the contrary the anomaly is acceptable and so winding can be restarted (return to step 102). At the end of the winding operation, an analysis report may be issued mentioning the anomalies that were recognized and those that were repaired. Advantageously, the report may be in the form of a representation of the casing in three dimensions as shown in FIG. 6A or in developed form as shown in FIG. 6B, with the various anomalies, whether or not they are repaired, appearing in their respective positions together with their order numbers. This graphical representation provides better visibility of anomaly repairs and of anomaly types. This leads to a significant saving of time in the cycle of processing departures from specification by enabling decisions to be taken more quickly. The possibility of comparing (superposing) the map of anomalies (weaving and/or winding anomalies) obtained by means of the invention with a map of faults observed when performing ultrasound monitoring constitutes an additional advantage.

The invention claimed is:
1. A method of determining weaving anomalies in a machine for weaving or winding a fiber preform onto a mandrel having an axis of rotation that is substantially horizontal for receiving the preform, the mandrel being driven about the axis of rotation by a motor actuated by a control unit; said method comprising:
scanning and acquiring images, with a plurality of cameras looking at the underside of the fiber texture, of the bottom face of the fiber preform,
processing, with an image analysis module, the images of the bottom face of the fiber preform in a plurality of adjacent scan windows in order to extract weaving patterns therefrom,
comparing said weaving patterns with reference weaving patterns previously stored in the module, stopping, with the control unit, rotation of the mandrel if the result of the comparison reveals, in at least one scan window, a difference in appearance between the two weaving patterns that is characteristic of the presence of an anomaly resulting from pollution and/or weaving faults in the fiber preform, and wherein, when an anomaly is recognized, its position on the fiber preform and a label selected by an operator from predetermined types of anomaly are stored together with an image of said anomaly, and when the recognized anomaly is repaired, a corresponding label selected by an operator from predetermined types of repair is stored together with an image of said repair, and the recognized anomalies and the repaired anomalies are displayed in a developed representation or a three-dimensional representation of said fiber preform that is accessible to the operator from said control unit.

2. The method according to claim 1, wherein the sizes, the positions, and the number of scan windows are defined by the operator directly on images coming from the cameras.

3. The method according to claim 2, wherein the number of scan windows corresponds at most to the number of cameras pointing towards the fiber preform.

4. The method according to claim 3, wherein the cameras are mounted in a light box adapted to match the profile of said mandrel and placed as close as possible to said fiber preform, the light box delivering blue light at a wavelength lying in the range 446 nm to 500 nm, or red light at a wavelength lying in the range 620 nm to 800 nm.

5. The method according to claim 1, wherein said appearance difference results from examining gray level curves for the images from the cameras.

6. The method according to claim 5, wherein said examination is performed in each of the scan windows along at least one detection line.

7. The method according to claim 5, wherein said examination is performed in each of the scan windows over a predefined detection area.

8. The method according to claim 1, wherein said mandrel is a pull mandrel of a loom.

9. The method according to claim 1, wherein said mandrel is an impregnation mandrel of a winding machine.

10. The method according to claim 1, wherein said representation of said fiber preform is superposed with a map of faults observed when performing ultrasound monitoring.

* * * * *